| United States Patent [19] | [11] | 4,268,310 |
|---|---|---|
| Nemeth | [45] | May 19, 1981 |

[54] DENTAL COMPOSITIONS OF IMPROVED PROPERTIES

[75] Inventor: William R. Nemeth, Highland Heights, Ohio

[73] Assignee: Diamond Shamrock Corporation, Dallas, Tex.

[21] Appl. No.: 144,605

[22] Filed: Apr. 28, 1980

[51] Int. Cl.$^3$ .............................................. B28B 7/34
[52] U.S. Cl. .................................. 106/38.35; 106/35; 106/111; 433/213
[58] Field of Search .................. 106/38.5 D, 38.5 R, 106/116, 111, 38.35, 35; 433/213, 214

[56] References Cited

U.S. PATENT DOCUMENTS

| 2,913,346 | 11/1959 | Hoffman | 106/88 |
|---|---|---|---|
| 2,941,890 | 6/1960 | Zandberg et al. | 106/38.3 |
| 3,369,915 | 2/1968 | Lee | 106/111 |
| 4,102,697 | 7/1980 | Fukuba et al. | 106/111 |
| 4,137,088 | 1/1979 | Debus et al. | 106/111 |
| 4,184,887 | 1/1980 | Lange et al. | 106/111 |

*Primary Examiner*—Lorenzo B. Hayes
*Attorney, Agent, or Firm*—Helen P. Brush

[57] ABSTRACT

A dental gypsum composition having good pourable consistency and controlled mixing and setting characteristics comprising a mixture of calcium sulfate hemihydrate (calcined gypsum), a condensation product of formaldehyde with a cyclic hydrocarbon containing sulfonic acid groups, and magnesium aluminum silicate. When dispersed in water and cured, this composition provides set products having improved hardness and strength properties.

10 Claims, No Drawings

DENTAL COMPOSITIONS OF IMPROVED PROPERTIES

BACKGROUND OF THE INVENTION

The present invention relates to dental materials derived from gypsum and, more particularly, relates to dental stone or plaster compositions having improved hardness and strength properties when set.

Dental gypsum materials, identified chemically as calcium sulfate hemihydrate $(CaSO_4)_2.H_2O$, are commercially obtained by calcining pulverulent natural gypsum, calcium sulfate dihydrate, $CaSO_4.2H_2O$, either in air or under steam pressure at temperatures of 110°–130° C. If calcination is carried out in air, the hemihydrate product obtained is composed of long, needlelike crystals which are irregular in shape and comparatively porous in nature. This product is known generally as beta gypsum or dental plaster. If, however, the calcination is conducted under steam pressure in an autoclave, the resulting hemihydrate product is composed predominately of cleavage fragments and crystals in the form of rods or prisms. The autoclaved product is denser and less porous than the beta hemihydrate and is designated for convenience as alpha gypsum, or dental stone. There are, in turn, two types of commercial dental stone, as classified by the American Dental Association, Type III stone; and Type IV stone or dental stone, high strength. For purposes of convenience, these products may be referred to hereinafter as "buff" stone and "die" stone, respectively. The latter is the most highly refined grade of autoclaved gypsum and is used when positive molds or cast masters having optimum detail rendition are to be prepared. Buff stone, on the other hand, is a cheaper grade of autoclaved gypsum and yields products which are correspondingly inferior propertywise to those from the die stone.

Although gypsum-water mixtures such as the foregoing have heretofore provided hardened products with a number of desirable properties, these products oftentimes have exhibited inferior hardness and/or strength. This is because, in hardening, they have occluded a significant portion of the gauging water used in their preparation. By "gauging water" is meant that quantity of water in addition to the water of reaction which is needed to impart flowable consistency to a gypsum dispersion. In efforts to reduce the quantity of gauging water so as to produce stronger finished products, it has become common practice in the art to incorporate various modifying additives into the basic gypsum-water formulations. Noteable among such additives are various types of surfactants or superplasticizers. Specific surfactants so employed are a class of modified polycondensation products of formaldehyde and aryl or heterocyclic hydrocarbons, which products contain sulfonic acid groups. These are used typically in the form of neutral salts. For example, U.S. Pat. No. 2,941,890 (Zandberg et al.) describes a method for reducing the gauging water required in water dispersions of gypsum by incorporating therein a neutral sodium salt of a condensed aryl sulfonic acid as the sole dispersing agent or surfactant.

However, the use of such surfactants in gypsum dispersions has oftentimes proven unsatisfactory in consumer applications. While the overall water requirements have thus been reduced, the resulting dispersions have been too thin and difficult to handle. Foaming due to the presence of air bubbles has likewise been a problem.

SUMMARY OF THE INVENTION

It is an object of this invention, therefore, to provide easily pourable dental gypsum aqueous dispersions of significantly reduced gauging water content which dispersions have a satisfactory final consistency when prepared, but will become fluid and pourable under vibration.

It is a further object of this invention to provide dental gypsum dispersions from which cured products having improved hardness and strength properties can be prepared.

It is still another object of this invention to provide a method for preparing an easily pourable dental gypsum-water composition of controlled mixing and setting characteristics.

These and other objects of this invention are accomplished by admixing a dental gypsum powder with water and, as the plasticizing component, a modified condensate of formaldehyde with an aryl or heterocyclic hydrocarbon sulfonic acid in combination with magnesium aluminum silicate. The hardened products produced from this composition are characterized by excellent surface smoothness and optimum hardness and strength.

DESCRIPTION OF THE PREFERRED EMBODIMENTS

The term "dental gypsum" employed herein in the specification and claims is, as indicated previously, intended to refer to those materials used in dentistry which are derived by calcining nearly pure calcium sulfate dihydrate, i.e., gypsum, at temperatures of 110°–130° C. to drive off part of the water of crystallization. Thus, the calcium sulfate hemihydrates, the aforedescribed dental plaster and dental stone materials, are both included in the scope of this invention, the chemical and physical properties of these products being improved thereby. Materials which consist predominately of completely anhydrous calcium sulfates, i.e., the anhydrites, are not included in this invention.

Further, the designation "condensation product of formaldehyde and a cyclic hydrocarbon containing sulfonic groups" as generally used herein in the specification and claims refers to normally solid, low molecular weight polymers obtained by condensing formaldehyde with an aryl sulfonic acid, such as naphthalene sulfonic acid or with a sulfonic acid of a heterocyclic hydrocarbon such as melamine. Preferably used herein in the form of neutral salts, these products have long been used to provide stable dispersion properties to wettable powder and flowable formulations and, as indicated previously herein, as additives for reducing the gauging water requirements of gypsum dispersions.

According to this invention, there is provided an improved dental gypsum composition which comprises calcined gypsum in combination with (1) a modified condensation product of formaldehyde and either an aryl or heterocyclic hydrocarbon containing sulfonic acid groups; and (2) magnesium aluminum silicate. Preferably, this mixture is in the form of a homogeneous powder to which the dental practitioner need only add the prescribed quantity of water to form a flowable dispersion. The dispersion can be cast into the particular dental impression or molding desired. The advantages of utilizing the composition in powder form at the site of application can be easily recognized from the standpoint of convenience and the savings in time and equipment which can be realized. Alternatively, of course, the surfactant and the magnesium aluminum silicate may be added to the gypsum material at the time when dental moldings are being prepared. In such instances, it is preferable to first incorporate the additives into the quantity of water to be employed in the dispersion, and then to add the additive-containing water to the gypsum with adequate spatulation. The manner of mixing the composition is not especially critical, and other methods for combining the components therein will become apparent to those skilled in the art. It is to be understood that any convenient method may be employed, providing an easily pourable homogeneous mixture of the components can be finally obtained with adequate spatulation.

The surfactant additive of this invention which is a modified condensate of formaldehyde and an aryl, e.g., napthalene sulfonic acid, is selected from a class of low molecular weight, polymer-type dispersing agents available commercially either as aqueous solutions or as light-colored powders. Presently, the powders are used in preferred embodiments herein. These surfactants are prepared by heating formaldehyde and an aryl hydrocarbon such as naphthalene with one or more sulfonic acids derived from various petroleum cracking processes to yield water and the acid form of the condensate. This product then is at least partially neutralized with a metal hydroxide such as sodium or potassium hydroxide, with zinc oxide, or with ammonia to give the neutral condensate salts commercially available. For purposes of convenience, these materials are designated hereinafter as alkylene naphthalene sulfonates. Their basic structural unit contains two naphthalene sulfonic acid salt rings joined by a methylene group. As the molecular weight of different commercially available members in this class of materials may vary, e.g., from about 800 to 1800, many of the aforesaid naphthalene sulfonic acid salt rings are joined together by methylene groups in the molecular structure of these polymers. A number of companies market condensed naphthalene sulfonates under various tradenames.

Another class of surfactant additives useful in the composition of this invention are polymer-type modified condensates of an aldehyde, e.g., formaldehyde, with a heterocyclic compound such as melamine. Designated hereinafter as alkylene melamine sulfonates for purposes of convenience, these additives may be obtained by condensing the aldehyde and melamine with sulfuric acid, followed by neutralization. They are available either as syrupy liquids of lower molecular weight or in the form of white powders of higher molecular weight. These latter solid products nevertheless are sufficiently water-soluble for the purposes of this invention. Melamine sulfonate condensates are commercially available at the present time.

The other additive component in the dispersing or plasticizing system of the improved dental gypsum composition of this invention is magnesium aluminum silicate. A natural mineral product of high magnesium content, this component is employed typically in the form of soft, white flakes that swell and disperse in water, forming a milky fluid. It is obtained by drying and flaking highly purified colloidal fractions of water slurries of mineral ores which are predominately saponite.

In preparing hardened gypsum products, approximately 18.63 grams of water for each 100 grams of unmodified hemihydrate will effect conversion to the dihydrate. However, gypsum-water mixtures in these ratios normally are moist, stiff masses or pastes so that additional water must be incorporated to attain workable consistency therein. The additional water that is required, defined herein above as "gauging water," will, of course, vary in quantity depending upon the type of calcined gypsum employed. Sufficient gauging water must usually be added to unmodified alpha gypsum hemihydrate to provide in the final mix an overall water to gypsum powder ratio (W/P) of 0.25 to 0.35, i.e., a ratio of from 25 to 35 cc's of water/100 grams of gypsum. To attain working or pourable consistency of unmodified beta gypsum hemihydrate dispersions, sufficient gauging water must be added to provide an overall W/P ratio of 0.45 to 0.55 in the final mix.

It has already been described herein that dental gypsum materials modified by surfactants such as the aforesaid polymeric condensates require substantially less gauging water to attain pourable consistency than do the unmodified gypsums. For satisfactory consumer application, the surfactant modified gypsums should be readily mixed and thoroughly dispersed in water within a reasonable time period as, e.g., with about 2 minutes of spatulation. It has been found, however, that even with the use of the proper quantity of gauging water to provide pourable consistency in the desired time period, surfactant modified gypsum-water mixtures are oftentimes rapidly converted from a thick pastelike consistency to that of a thin soupy dispersion. This is messy, difficult to contain during pouring operations, and a substantial quantity of the gypsum material can be wasted. Magnesium aluminum silicate is incorporated in the modified gypsum dispersion to impart thereto the more bodied final consistency desired for easier handling, but without altering its degree of fluidity under vibration. A bodied consistency deemed desirable is similar to that of egg whites, for example, beaten to "peaking" consistency, and the terms "peaking" or "peaked" as may be used herein are intended to refer to the consistency attained in the gypsum dispersions by the incorporation of the magnesium aluminum silicate. In dental operations, dispersions of the improved dental gypsum composition of this invention accordingly can be prepared in reasonable time periods to a satisfactory peaked consistency at which they can be easily contained with no handling difficulties or material waste. Upon being vibrated, these dispersions become completely pourable and flow into and fill intricate molds with optimum detail rendition. The finished moldings exhibit excellent texture and surface smoothness as well as good hardness and strength characteristics.

In processing the modified dental gypsum composition of this invention, the gauging water requirement may be reduced up to 50 percent from that of the unmodified material, without any appreciable loss of workability. These dispersions, in turn, produce molded products which may exhibit hardness increases of up to 60 percent over those from the unmodified gypsums, with improvements of 30 to 40 percent in compressive strength.

In general, the dental gypsum compositions of this invention contain about 0.2 to 1.0 percent, by weight, of the condensed aryl or heterocyclic hydrocarbon sulfonate surfactant modifier; and about 0.10 to 0.25 percent, by weight, of the magnesium aluminum silicate. At present, about 0.4 to 0.8 percent, by weight, of surfactant and about 0.15 to 0.20 percent, by weight, of the silicate are employed in preferred embodiments herein.

The improved compositions of this invention offer to the dental practitioner a gypsum molding composition useful both in casting and molding operations, mixes well in a reasonable time period, is easily handled or manipulated either manually or mechanically, has a desirable consistency, and is substantially free from air bubbles after spatulation. Further possessing controlled setting characteristics, this composition can be directed into all parts of an impression easily with exact reproduction of minutest details.

In order that those skilled in the art may more completely understand the present invention and the preferred method for carrying it into effect, the following specific examples are offered.

EXAMPLE 1

To establish the water to powder ratio (W/P) essential for providing pourable or vibratable "peaked" consistency to dental gypsum slurries, the testing consistency of various unmodified gypsum-water mixtures was determined by the cone penetration method, using the modified Vicat apparatus, according to the American Dental Association Specification No. 25 for dental gypsum products. Testing consistency is defined as the W/P ratio which provides the required cone penetration depth of 30±2 mm for Types III and IV dental stone specimens, by applying 100 g total plunger weight, as set forth in the specification.

For the test, 300 g of unmodified plaster or stone was added to a known volume of 1 percent sodium citrate solution in distilled water in a 10 to 13 cm diameter plastic mixing bowl. The mixture was allowed to soak for 30 seconds and was then stirred for 1 minute to a smooth consistency with a round-ended, stiff-bladed spatula at the rate of 120 rpm. The mixed sample was poured into a ring mold, vibrated to remove air bubbles and then struck off flush with the top of the mold. Using an additional weight to provide 100 g total weight to the plunger assembly, penetration readings were determined at 7, 8, and 9 minutes after the start of mix. The average of the three penetration readings taken provided the measure of the consistency. Using this procedure, the following ml of water were required to provide a cone penetration depth of 30±2 mm to test samples of Type III and Type IV dental stone.

TABLE 1

| Run No. | Formulation | Ml Water/ 100 g Stone | Penetration mm | W/P Ratio |
|---|---|---|---|---|
| 1 | Type III (Buff stone) | 31.0 | 30.0 | 0.31 |
| 2 | Type IV (Die stone) | 24.0 | 30.0 | 0.24 |

The peaked consistency of modified Type III dental stone compositions of this invention was determined following the same procedure employing, in each instance, 100 g total weight on the plunger assembly. In each test formulation, quantities of dental gypsum and the additive together equalled 300 g. Results obtained were as follows:

TABLE 2

| Run No. | Formulation Type III Stone Base Additive | Ml H₂O/ 100 g Stone | Average Penetration mm | % Reduction/ Gauging Water |
|---|---|---|---|---|
| 3 | 2.4 g Surfactant No. 1[a] | 27.0 | 33.2 | 32.3 |
| 4 | 2.4 g Surfactant No. 1[a] | 26.0 | 28.83 | 40.4 |
| 5 | 2.4 g Surfactant No. 1 0.45 g Mg Al Silicate | 26.0 | 22.33 | 40.4 |
| 6 | 2.4 g Surfactant No. 1 0.45 g Mg Al Silicate | 26.7 | 22.67 | 34.2 |
| 7 | 2.25 g Surfactant No. 2[b] | 26.3 | 31.3 | 38.0 |
| 8 | 2.25 g Surfactant No. 2[b] | 26.6 | 34.5 | 35.6 |
| 9 | 2.25 g Surfactant No. 2 0.45 g Mg Al Silicate | 26.6 | 23.67 | 35.6 |
| 10 | 2.25 g Surfactant No. 2 0.45 g Mg Al Silicate | 26.0 | 18.67 | 40.4 |

[a]Surfactant No. 1 - Commercial Alkylene Naphthalene Sulfonate, Sodium Salt.
[b]Surfactant No. 2 - Commercial Alkylene Melamine Sulfonate, Sodium Salt.

The above results illustrate the effect of using magnesium aluminum silicate. Mixes of modified dental stone containing either alkylene naphthalene sulfonate or alkylene melamine sulfonate were made corresponding in consistency to the standard unmodified dental stone. In all instances, the water volume requirements were reduced. By adding magnesium aluminum silicate to these same formulations while maintaining the same W/P ratios, the consistency of the resulting further modified compositions was substantially greater, as shown by the reduced penetration depth. By use of the magnesium aluminum silicate, a modified gypsum formulation can be prepared which has a much greater gel strength than that containing only a surfactant. This formulation nevertheless has the necessary fluidity under manipulation to fill the most intricate molds with excellent detail rendition.

EXAMPLE 2

This example further illustrates that modified dental gypsum compositions according to this invention have a gel consistency approximating that of unmodified gypsum compositions, while the volume of water required to provide fluidity thereto is similar to that needed in dental gypsum compositions containing surfactant but no magnesium aluminum silicate.

Formulating both dental plaster and Type III and Type IV dental stone compositions, the procedure employed was similar to that outlined in Example 1 above using the modified Vicat apparatus described. For this test, however, the conical ring mold was employed inverted from the procedure of Example 1 so that the inside diameter was 7 cm at the base and 6 cm at the top. Using distilled water, each 300 g total solids formulation was mixed as set forth in Example 1. It was then placed in the inverted mold and struck level. The tip of the plunger assembly was brought to the surface of the mix, and the scale was read and recorded. Three minutes from the time of starting the mix, the ring mold was lifted slowly, allowing the then unconfined mixture to spread (or slump). The plunger was brought to the surface of the slumped mixture, and the scale read and recorded. The millimeter difference obtained between the first and second readings for each formulation, i.e., the slump, as a measure of its fluidity, compared to the fluidity readings of other formulations. Noticeable differences in fluidity of different formulations were observed although the W/P ratios required for pourability of these may have been approximately the same when measured according to the consistency test of Example 1.

Using this procedure, the following average results were obtained:

TABLE 3

| Run No. | Dental Gypsum Base | Additive | Additive (g) | Ml Water Used | Slump (mm) |
|---|---|---|---|---|---|
| 1 | Type III Stone | — | — | 93.0 | 5.5–6.0 |
| 2 | | Alkylene Naphthalene Sulfonate[a] | 2.4 | 79.0 | 18.5 |
| 3 | | Alkylene Naphthalene Sulfonate + Magnesium Al Silicate | 2.4 0.45 | 79.0 | 8.5 |
| 4 | | Alkylene Naphthalene Sulfonate + Magnesium Al Silicate | — | 78.0 | 6.5 |
| 5 | | Alkylene Melamine Sulfonate[b] | 2.25 | 79.0 | 23.5 |
| 6 | | Alkylene Melamine Sulfonate[b] | — | 78.0 | 19.5 |
| 7 | | Alkylene Melamine Sulfonate + Magnesium Al Silicate | 2.25 0.45 | 79.0 | 10.0 |
| 8 | | Alkylene Melamine Sulfonate + Magnesium Al Silicate | — | 78.0 | 7.0 |
| 9 | Type IV Stone | — | — | 73.0 | 6.0 |
| 10 | | Alkylene Melamine Sulfonate | 2.25 | 58.0 | 30.0 |
| 11 | | Alkylene Melamine Sulfonate + Magnesium Al Silicate | 2.25 0.45 | 58.0 | 7.5 |
| 12 | | Alkylene Naphthalene Sulfonate | 1.5 | 58.0 | 15.0 |
| 13 | | Alkylene Naphthalene Sulfonate + Magnesium Al Silicate | 1.5 0.45 | 58.0 | 7.0 |
| 14 | Plaster | — | — | 135.0 | 5.0 |
| 15 | | Alkylene Naphthalene Sulfonate | 3.0 | 116.0 | 6.0 |
| 16 | | Alkylene Naphthalene Sulfonate + Magnesium Al Silicate | 3.0 0.45 | 116.0 | 4.0 |
| 17 | | Alkylene Melamine Sulfonate | 3.0 | 116.0 | 10.0 |
| 18 | | Alkylene Melamine Sulfonate + Magnesium Al Silicate | 3.0 0.45 | 116.0 | 6.0 |

TABLE 3-continued

| Run No. | Dental Gypsum Base | Additive | Additive (g) | Ml Water Used | Slump (mm) |
|---|---|---|---|---|---|
| | | Magnesium Al Silicate | 0.45 | | |

[a,b]Surfactants described previously.

Of the foregoing formulations, those containing surfactant and magnesium aluminum silicate were found to possess a more favorable gel consistency than those containing the surfactant alone. This favorable gel consistency, which approximated that of the unmodified gypsum product, was obtained merely by using the magnesium aluminum silicate without increasing the W/P ratio from that of the compositions containing surfactant alone.

EXAMPLE 3

This example illustrates the improved properties obtained in moldings prepared from compositions of this invention wherein the calcined gypsum base is the beta hemihydrate or dental plaster.

For each molding, 100 g of plaster was placed in a glass jar. To the jar were added 1 g of the surfactant and 0.15 g of magnesium aluminum silicate, as indicated in the following table. The jar was then capped and the contents thoroughly mixed by tumbling. The volume of water necessary to attain pourable slurry consistency was measured into a mixing apparatus. The plaster-additive mixture was sifted into the water and mixed to a dispersion of smooth, even consistency by thorough spatulation for 90 seconds. After being quickly vibrated to eliminate air bubbles, the prepared dispersion was placed in a weigh boat and vibrated briefly to flow material evenly. As a control, a 100 g sample of plaster was mixed with the necessary volume of water for pourable slurry consistency, vibrated and placed in an open molding for setting.

Additional formulations similarly prepared were poured into split molds to form cylindrical specimens 20 mm in diameter and 40 mm high for compressive strength testing according to A.D.A. Specifications. These were also stored for 3 days before testing.

The first prepared specimens were tested for hardness using the ASTM Standard E18 Rockwell Superficial Hardness test using a ⅛-inch steel ball as penetrator. The cylindrical specimens were tested on the Instron Testing Machine (Model 1123), loading at a rate of 0.25 cm/min. Results are as follows:

TABLE 4

| Formulation | Surfactant | Pourable Consistency Water/Ml | Compressive Strength Kg/Cm$^2$ | Rockwell Hardness |
|---|---|---|---|---|
| Plaster Control | — | 45 | 293.9 | 24.0 |
| Plaster + Magnesium Al Silicate | Alkylene Naphthalene Sulfonate[a] | 38 | 426.4 | 29.4 |
| Plaster + Magnesium Al Silicate | Alyklene Melamine Sulfonate[b] | 38 | 471.0 | 32.8 |

[a]As described previously.
[b]As described previously.

As these results show, moldings of modified dental plaster compositions according to this invention possess significantly improved strength and hardness properties compared to those of unmodified plaster.

EXAMPLE 4

Following the same general procedure as set forth in Example 3 above, moldings were prepared of Type III dental stone using 100 g of the stone, 0.20 g of magnesium aluminum silicate and the quantity of surfactant shown below in the table. After preparation, the moldings were stored for 4 days prior to testing. The moldings exhibited the following properties:

TABLE 5

| Formulation | Surfactant | Pourable Consistency Water/Ml | Compressive Strength $Kg/Cm^2$ | Rockwell Hardness |
| --- | --- | --- | --- | --- |
| Type III Dental Stone | — | 30 | 581.0 | 61.4 |
| Dental Stone + Magnesium Al Silicate | Alkylene Melamine Sulfonate-0.75 g | 24 | 710.2 | 82.2 |
| Dental Stone + Magnesium Al Silicate | Alkylene Naphthalene Sulfonate-0.8 g | 24 | 688.7 | 71.2 |

Following the same general procedure, moldings were prepared of Type IV dental stone, using 100 g of the stone, 0.15 g of magnesium aluminum silicate and surfactant as shown below. The prepared moldings exhibited the following hardness properties:

TABLE 6

| Formulation | Surfactant | Pourable Consistency Ml Water | Rockwell Hardness |
| --- | --- | --- | --- |
| Type IV Stone | — | 24 | 128.8 |
| Stone + Magnesium Al Silicate | Alkylene Melamine Sulfonate-0.75 g | 19 | 161.6 |
| Stone + Magnesium Al Silicate | Alkylene Naphthalene Sulfonate-0.5 g | 19 | 133.9 |

As the above results indicate, the hardness and/or strength properties of the modified dental gypsum compositions of this invention are significantly improved over those of the unmodified gypsum.

What is claimed is:

1. A dental composition consisting essentially of calcined gypsum, magnesium aluminum silicate, and a surfactant selected from the group consisting of a condensation product of formaldehyde and naphthalene sulfonic acid and a condensation product of formaldehyde and melamine sulfonic acid.

2. The dental composition of claim 1 wherein the calcined gypsum is alpha calcium sulfate hemihydrate.

3. The dental composition of claim 1 wherein the calcined gypsum is beta calcium sulfate hemihydrate.

4. The dental composition of claim 1 wherein the surfactant is a condensation product of formaldehyde and naphthalene sulfonic acid.

5. The dental composition of claim 1 wherein the surfactant is a condensation product of formaldehyde and melamine sulfonic acid.

6. The dental composition of claim 1 which contains from about 0.10 to 0.25 percent, by weight, of magnesium aluminum silicate and from about 0.20 to 1.0 percent, by weight, of surfactant.

7. The dental composition of claim 6 which contains from about 0.15 to 0.20 percent, by weight, of magnesium aluminum silicate and from about 0.4 to 0.8 percent, by weight, of surfactant.

8. A method of reducing the amount of water required to be mixed with a dental powder to obtain a pourable slurry which comprises adding to a calcined gypsum from about 0.10 to 0.25 percent, by weight, of magnesium aluminum silicate and from about 0.20 to 1.0 percent, by weight, of a surfactant selected from the group consisting of a condensation product of formaldehyde and naphthalene sulfonic acid and a condensation product of formaldehyde and melamine sulfonic acid.

9. The method of claim 8 wherein the magnesium aluminum silicate and surfactant are added to the gypsum.

10. The method of claim 8 wherein the magnesium aluminum silicate and surfactant are incorporated into the volume of water to be used to slurry the gypsum prior to its admixture with said gypsum.

* * * * *